US00PP12156P2

(12) United States Plant Patent
Slaughter et al.

(10) Patent No.: US PP12,156 P2
(45) Date of Patent: Oct. 23, 2001

(54) PEACH TREE NAMED 'BURPEACHONE'

(75) Inventors: John K. Slaughter, Clovis; Timothy J. Gerdts, Kingsburg, both of CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 09/461,135

(22) Filed: Dec. 13, 1999

(51) Int. Cl.[7] ..... A01H 5/00
(52) U.S. Cl. ..... Plt./197

(58) Field of Search ..... Plt./197

*Primary Examiner*—Bruce R. Campell
*Assistant Examiner*—Susan B. McCormick
(74) *Attorney, Agent, or Firm*—Wells, St. John, Roberts, Gregory & Matkin P.S.

(57) ABSTRACT

A new and distinct variety of peach tree denominated varietally as 'Burpeachone', and which is characterized as to novelty by producing an attractively colored fruit which is ripe for commercial harvesting and shipment approximately May 17 to May 23 under the ecological conditions prevailing in the San Joaquin Valley of central California.

1 Drawing Sheet

BACKGROUND OF THE NEW VARIETY

The present invention relates to a new, novel and distinct variety of peach tree, which has the denominated varietally as 'Burpeachone'. The 'Burpeachone' Peach Tree produces an exceptionally high quality, peach which is mature for harvesting and shipment in the early season. Another unique aspect of the 'Burpeachone' is that it yields a very firm peach that has a high eating quality.

ORIGIN

The present variety of peach tree resulted from an ongoing program of fruit and nut tree breeding. The purpose of this program is to improve the commercial quality of deciduous fruit and nut varieties and rootstocks by creating and releasing promising selections of *prunus, malus* and *regia* species. To this end, we make both controlled and hybrid crosses each year in order to produce seedling populations from which improved progenies are evaluated and selected. The seedling 'Burpeachone' was originated by us in 1994, and was chosen from among a population of seedlings which resulted from a controlled cross from two selected parents. The female parent was an early ripening peach of unknown parentage, and the pollen parent was the 'Rich Lady' Peach Tree (U.S. Plant Pat. No. 7,290). The resulting seed from this controlled cross was planted in the spring of 1995. The new variety was selected from among seedlings growing in the experimental orchards of the assignee which are located near the city of Fowler, Calif., County of Fresno, in the central portion of the San Joaquin Valley of California. The Peach Tree 'Burpeachone' was subsequently marked for observation and noted as having exceptional characteristics. It has subsequently been evaluated during the 1997–2000 fruiting seasons. After the 1996 season, 'Burpeachone' was selected for advanced evaluation and repropagation.

ASEXUAL REPRODUCTION

The new variety of Peach Tree 'Burpeachone' was grafted into two different and existing 'Nemared' peach (unpatented) rootstocks in February of 1997. The Nemagrand rootstocks were planted in January of 1995 in order to provide a site from which more information of the new variety could be derived. Scionwood from the original seedling of the Peach Tree, 'Burpeachone' was collected and grafted in the evaluation plot on assignee's experimental farm previously described. Fruit from the resulting propagation has been evaluated for the 1998 and 1999 fruiting seasons, and this subsequent evaluation clearly demonstrated that the repropagated trees are true to the characteristics of the original seedling in all observable aspects.

SUMMARY OF THE VARIETY

The 'Burpeachone' Peach Tree is characterized as to novelty by producing early season fruit having a very high quality; which are very firm; and which also have an attractive exterior coloration. In this regard, the present variety of peach tree bears fruit which are ripe for commercial harvesting and shipment on approximately May 17 to May 23. These harvest dates are substantially similar to the harvest dates of the commercial peach variety the 'May Crest' Peach Tree (U.S. Plant Pat. No. 4,064). The present variety of peach tree distinguishes itself from the 'May Crest' Peach Tree by producing fruit which have a brighter exterior coloration, are more flavorful and has a firmer flesh. Further, the 'Burpeachone' Peach Tree distinguishes itself from the 'May Crest' Peach Tree in that the fruit of the 'May Crest' Peach Tree has a background color that can vary from a greenish to yellow-green hue, while in contrast, the fruit produced by the 'Burpeachone' Peach Tree has a background color that is yellow-orange to an orange color.

BRIEF DESCRIPTION OF THE DRAWING

The accompanying drawing is a color photograph of a characteristic twig bearing typical leaves; several leaves showing both the dorsal and ventral coloration thereof; and several mature fruit displaying their external coloration sufficiently matured for harvesting and shipment. Additionally, one fruit of the subject variety is dissected in the equatorial or cheek plane to illustrate the flesh and stone characteristics thereof.

DETAILED DESCRIPTION

Referring more specifically to the pomological details of this new and distinct variety of peach tree, the following has been observed under the ecological conditions prevailing near the town of Fowler, Fresno county, state of California. All major color code designations are by reference to the R.H.S. Colour Chart (1995 Third Edition) provided by The Royal Horticultural Society of Great Britain.

Tree:

*Size.*—Generally — Average to above average as compared to other common peach cultivars.

*Productivity.*—Productive. Productivity, with respect pounds per acre, is not available.

*Figure.*—The original seedling was trained in a central leader configuration with a moderate spread in the crown of the tree. The tree is considered upright to upright spreading in form.

*Height.*—The original seedling had a height dimension of 9.5 ft (2.89 m) at the end of the 1999 growing season.

*Width.*—The original seedling tree had a 5.6 ft width (1.70 m) at the end of the 1999 growing season.

*Current season growth.*—The current season growth for the new variety was approximately 2.1 to 2.3 ft (0.63–0.70 m).

*Regularity of bearing.*—Regular, and considered hardy under typical central San Joaquin Valley climatic conditions.

*Lenticels.*—Length — 3–4 mm.

*Lenticels.*—Width — 1 mm.

*Lenticles.*—Color — Greyed Orange Group (177D).

Trunk:

*Diameter.*—Approximately 1.51 inches (38.3 mm) in diameter when measured at a distance of approximately six inches (15.24 cm) above the soil level, at the end of the 2000 growing season on a three year old grafted tree.

*Bark texture.*—Considered moderately rough with numerous folds of papery scarf skin being present.

*Lenticels.*—Numerous flat, oval lenticels are present. The lenticels range in size from approximately 3.0 to 7.0 millimeters in width, and from approximately 1 to 2 millimeters in height.

*Bark coloration.*—Variable, but it is generally considered to be a grey-brown (RHS Greyed-Orange Group 174 A).

Branches:

*Size.*—Considered medium for the variety.

*Diameter.*—The branches have a diameter of 52–57 mm when measured on the fourth year after grafting.

*Surface texture.*—Average, and appearing furrowed on wood which is several years old.

*Crotch angles.*—Variable between about 47° to 55° from the horizontal axis for scaffold limbs. This is not distinctive of the variety, however.

*Current season shoots.*—Surface Texture — Substantially glabrous.

*Internode length.*—Approximately 2.3 to 2.5 cm.

*Color of mature branches.*—Medium brown, (RHS Greyed Orange Group 175 C to 177 B).

*Current season shoots.*—Color — Light green, (RHS Yellow Green Group 144 C), with some reddish-brown coloration appearing on exposed exterior shoots (RHS Greyed Red Group 181 B). The color of the new shoot tips is considered a bright and shiny green (RHS Green Group 143B).

Leaves:

*Size.*—Considered average for the species. Leaf measurements have been taken from vigorous upright current season growth approximately at mid-shoot.

*Leaf length.*—Approximately 155 to 160 millimeters.

*Leaf width.*—Approximately 46 to 49 millimeters.

*Leaf thickness.*—Approximately 1 to 2 millimeters.

*Leaf base shape.*—The leaf base is slightly oblique.

*Leaf form.*—Lancelolate.

*Leaf tip form.*—Acuminate.

*Leaf color.*—Dark green, (RHS Yellow Green Group 147 A).

*Leaf texture.*—Substantially glabrous.

*Lower surface.*—Light green, (RHS Yellow Green Group 147 B).

*Venation.*—Pinnately net veined.

*Mid-vein.*—Color — Light yellow green, (RHS Yellow Green Group 150 D).

*Leaf margins.*—Form — Considered crenate, occasionally doubly crenate. Uniformity.— Considered generally uniform.

*Leaf petioles.*—Size — Considered medium. Length — Approximately 8 to 10 millimeters. Diameter — Approximately 1.5 to 2 millimeters. Color — Pale green, (RHS Yellow Green Group 150 C).

*Leaf glands.*—Size — Approximately one to two millimeters in height and two to three millimeters in width. Numbers — Generally 1–2 per side, occasionally two per side. Type — Reniform. Color — Greenish brown (RHS Grey Brown 199 C).

*Leaf stipules.*—Size — 7–11 mm in length; 1 mm in width. Number — Typically (2) stipules per leaf bud and up to (6) per shoot tip. Form — Linear in form with a serrated margin. Color — Green (RHS Green Group 135A) when young but changing to a to brown (RHS Greyed Orange Group 177A) color with advancing senescence. The stipules are considered to be early deciduous.

Flowers:

*Flower buds.*—Generally — The floral buds are considered to be medium in size (22–25 mm long), plump (15–18 mm wide) slightly pointed in form, and moderately free, relative to the bearing shoot.

*Flower buds.*—Color — The bud scales are gray-brown, (approximately RHS Greyed Orange Group 165 B). The buds are considered hardy, under typical central San Joaquin Valley climatic conditions.

*Hardiness.*—No winter injury has been noted during the several years of evaluation in the Central San Joaquin Valley. The current variety has not been intentionally subjected to drought or heat stress and therefore this information is not available.

*Date of first bloom.*—First bloom was observed on Feb. 23, 1998.

*Blooming time.*—Considered slightly early in relation to other peach cultivars commonly growing in the central San Joaquin Valley. Date of full bloom was observed on Feb. 27, 1998.

*Duration of bloom.*—Typically one to two weeks. This is influenced by ambient temperatures.

*Flower type.*—The variety is considered to be a showy type flower.

*Flower size.*—Flower diameter at full bloom is approximately 38 to 45 millimeters.

*Bloom quantity.*—Considered abundant.

*Flower bud frequency.*—Normally 1 to 2 buds appear per node, although 2 buds per node is more common.

*Petal size.*—Generally — Considered medium for the species. Length — Approximately 17 to 22 millimeters. Width — Approximately 16 to 20 millimeters.

*Petal shape.*—Broadly ovate.

*Petal count.*—Nearly always 5.

*Petal texture.*—Glabrous.

*Petal color.*—Light pink when young, (approximately RHS Red Purple Group 65 C), and with advancing senescence, the color changes to a very pale pink (RHS Red Purple Group 69 D). The lower portion of the flower petal is typically darker than the apical protions and exhibits medium pink coloration (RHS Red-Purple Group 62A).

*Fragrance.*—None to occasionally slight.

*Petal claw.*—Form — The claw is considered truncate in shape and has a medium size when compared to other similar varieties. Length — Approximately 2 to 3 millimeters. Width — Approximately 1 millimeter.

*Petal margins.*—Generally considered variable, from nearly smooth, to moderately undulate.

*Petal apex.*—Generally — The petal apices appear slightly domed.

*Flower pedicel.*—Length — Considered average to short, and having a length of approximately 2.0 to 3.0 millimeters. Diameter — Considered average, approximately 2 millimeters. Color — Bright green (RHS Yellow Green Group 144 D).

*Floral nectaries.*—Color — Dull orange to an orange-gold color, (approximately RHS Orange Red Group 31 A). The color of the nectaries become increasingly dull and slightly darker with advancing senescence.

*Calyx.*—Surface Texture — Generally glabrous, with slight ribbing. Color — A dull red, (approximately RHS Greyed Red Group 184 A).

*Sepals.*—Surface Texture — The surface has a medium length, wooly, and gray colored pubescence. Number — Generally 5 per flower. Size — Typically 4–5 mm wide and 5–6 mm in length and ovate in form. Color — A dull red (approximately RHS Greyed Red Group 178 A).

*Anthers.*—Generally — Average in size. Approximately 1.0 mm in width; and 1.0–1.5 mm in length. Color — Red to reddish-orange dorsally, (approximately RHS Greyed Purple Group 187 A). Pollen Production — Pollen is abundant, and has a yellow-gold color, (approximately RHS Yellow Orange 26 A).

*Filaments.*—Size — Variable in length, approximately 12 to 14 millimeters. Color — White, (RHS Red Purple Group 69 D), and darkening with advanced maturity.

*Pistil.*—Generally — Average in size. Length — Approximately 13 to 16 millimeters, including the ovary. Color — Considered a very pale green, at midbloom, (approximately RHS Yellow Green Group 154 D). Surface Texture — Pubescent.

Fruit:

*Maturity when described.*—The present variety of fruit is described, as it would be found in its firm ripe condition at full commercial maturity. In this regard, the fruit of the present variety was first picked on May 17, 1998. The date of last pick of the same fruit in 1998 was approximately May 23, 1998 under the ecological conditions prevailing in the San Joaquin Valley of Central California.

*Size.*—Generally — Medium in size, and considered uniform.

*Average cheek diameter.*—Approximately 75 to 78 millimeters.

*Average suture diameter.*—Approximately 75 to 79 millimeters.

*Average axial diameter.*—Approximately 74 to 77 millimeters.

*Typical weight.*—170 grams. This is highly dependent on cultural practices, and therefore is not distinctive of the present variety.

*Fruit form.*—Generally — Globose in its lateral aspect. The fruit is generally uniform in symmetry with a substantially rounded form when viewed from the apical aspect.

*Fruit suture.*—Generally — The suture appears as a thin line, which extends from the base to the apex. The suture appears slightly deeper, basally, within the stem well, and apically on both sides of the pistil point. No apparent callousing or stitching exists along the suture line.

*Color.*—The suture normally is the same color as the underlying blush, both where the orange-yellow background color, (RHS Yellow Group 24 C) and the red orange color (RHS Red Group 46 A to 46 B) occur.

*Ventral surface.*—Form — Considered uniform.

*Stem cavity.*—Size — Considered moderate for the species. Width — Approximately 18–20 millimeters. Length — Approximately 27–30 millimeters. Depth — Approximately 8 to 10 millimeters. Form — Considered narrowly oval. Fruit Base — Generally — Considered truncate in form, and uniform. Fruit Apex — Generally — Considered depressed and usually recessed below the height of the apical shoulders. Occasionally an extended apex will be noted.

*Fruit stem.*—Generally — Considered medium in length, approximately 8 to 9 millimeters. Diameter — Approximately 3 to 4 millimeters. Color — Generally a pale yellow-green (approximately RHS Yellow Green Group 145 B).

*Fruit skin.*—Generally — Considered average in thickness. Surface Texture — The variety has very short, light pubescent surface. Skin Acidity — Considered neutral.

*Tenacious to flesh.*—Yes at commercial maturity.

*Tendency to crack.*—Not observed.

*Skin color.*—Generally — Variable, with approximately 80% to 90% of the fruit surface covered with a brilliant crimson red blush.

*Blush color.*—The blush color is generally more prevalent apically. This red blush color ranges from a dark red, (RHS Red Orange Group 46 A to 46 B) to an orange red, (RHS 33 B), with many degrees of shading and blending between these colorations.

*Skin ground color.*—This is generally present in variable percentages covering approximately 10% to 20% of the fruit's surface. The skin ground color is a yellow-golden color (RHS Yellow Orange Group 22 A to 24 C).

*Flesh color.*—Generally — Considered variable from a yellow/orange, (RHS Yellow Orange Group 21 C to 21 A).

*Flesh fibers.*—Generally — Present, numerous, fine and light colored. These fibers are present throughout the flesh.

*Stone cavity.*—Color — Red, (approximately RHS Red Orange Group 45 B), to a yellow orange, (approximately RHS Yellow Group 18 B).

*Flesh texture.*—Generally — The flesh is considered firm and fine at full commercial maturity. The flesh texture is considered to be firm yet melting.

*Ripening.*—Generally — The fruit of the present variety ripens evenly.

*Flavor.*—This variety is considered very sweet and has moderate acidity. The flavor is considered both pleasant and balanced.

*Aroma.*—Pleasant and abundant.

*Eating quality.*—Generally — Considered very good to excellent and well above average when compared to other common peach tree varieties.

Stone:

*Attachment.*—Generally — The stone is considered to be a semi-freestone at full commercial maturity.

*Stone size.*—Generally — Considered medium-small for the species.

*Length.*—Approximately 27 to 30 millimeters.

*Width.*—Approximately 20 to 21 millimeters.

*Diameter.*—Approximately 19 to 21 millimeters.

*Fibers.*—Generally — A few medium length fibers are attached along the entire surface of the stone.

*Stone form.*—Generally — The stone is considered oval to slightly elongated.

*Stone base.*—The stone base is generally considered truncate.

*Base angle.*—The base angle of the stone is variable, but most frequently is considered oblique to the stone axis.

*Hilum.*—Generally — Considered medium in size, and relatively poorly defined. The hilum is approximately 4 to 6 millimeters long and approximately 3 to 4 millimeters wide.

*Form.*—Considered oval.

*Apex.*—Shape — The stone apex is raised and has an acute tip.

*Stone shape.*—Considered variable. The stone is normally unequal, although occasionally it may appear nearly equal.

*Stone surface.*—Surface Texture — Generally considered medium in roughness, and exhibits substantial pitting laterally. Substantial grooving is apparent over the apical shoulders. Surface pitting is prominent, generally, and is more frequently present basally.

*Ridges.*—Numerous fine ridges are present basally, and converge towards the base of the stone.

*Ventral edge.*—Width — Considered medium and prominent. The ventral edge has a dimension of approximately 5 to 6 millimeters at mid-suture. The wings are most prominent over the basal area.

*Dorsal edge.*—Full, heavily grooved and having jagged edges. The dorsal edge is moderately eroded over the apical shoulder.

*Stone color.*—The color of the dry stone is a light to medium brown, (RHS Orange Red Group 34 D).

*Tendency to split.*—Infrequent splitting noted.

*Kernel.*—Kernel is gelatinous and immature when fruit is ripe.

*Use.*—The subject variety 'Burpeachone' is considered to be a peach which matures in the early season, and which is very firm, has an attractive exterior color, and which is useful for both local and long distance shipping.

*Keeping quality.*—Fruit has stored well up to 20 days after harvest at temperatures of about 2° C.

*Resistance to insects and disease.*—No particular susceptibilities were noted.

*Shipping quality.*—Suitable for local and long distance shipping.

Although the new variety of peach tree possesses the described characteristics noted above, as a result of the growing conditions prevailing in the central part of the San Joaquin Valley of central California, it is to be understood that variations of the usual magnitude and characteristics incident to growing conditions, fertilization, pruning, and pest control are to be expected.

Having thus described and illustrated our new Peach tree variety, what we claim is new and desire to secure by Plant Letters Patent is:

1. A new and distinct variety of peach tree 'Burpeachone', substantially as illustrated and described and which is characterized as to novelty by producing an attractively colored semi-freestone peach which is sufficiently matured for harvesting and shipment approximately May 17 to May 23 under the ecological conditions prevailing in the San Joaquin Valley of central California.

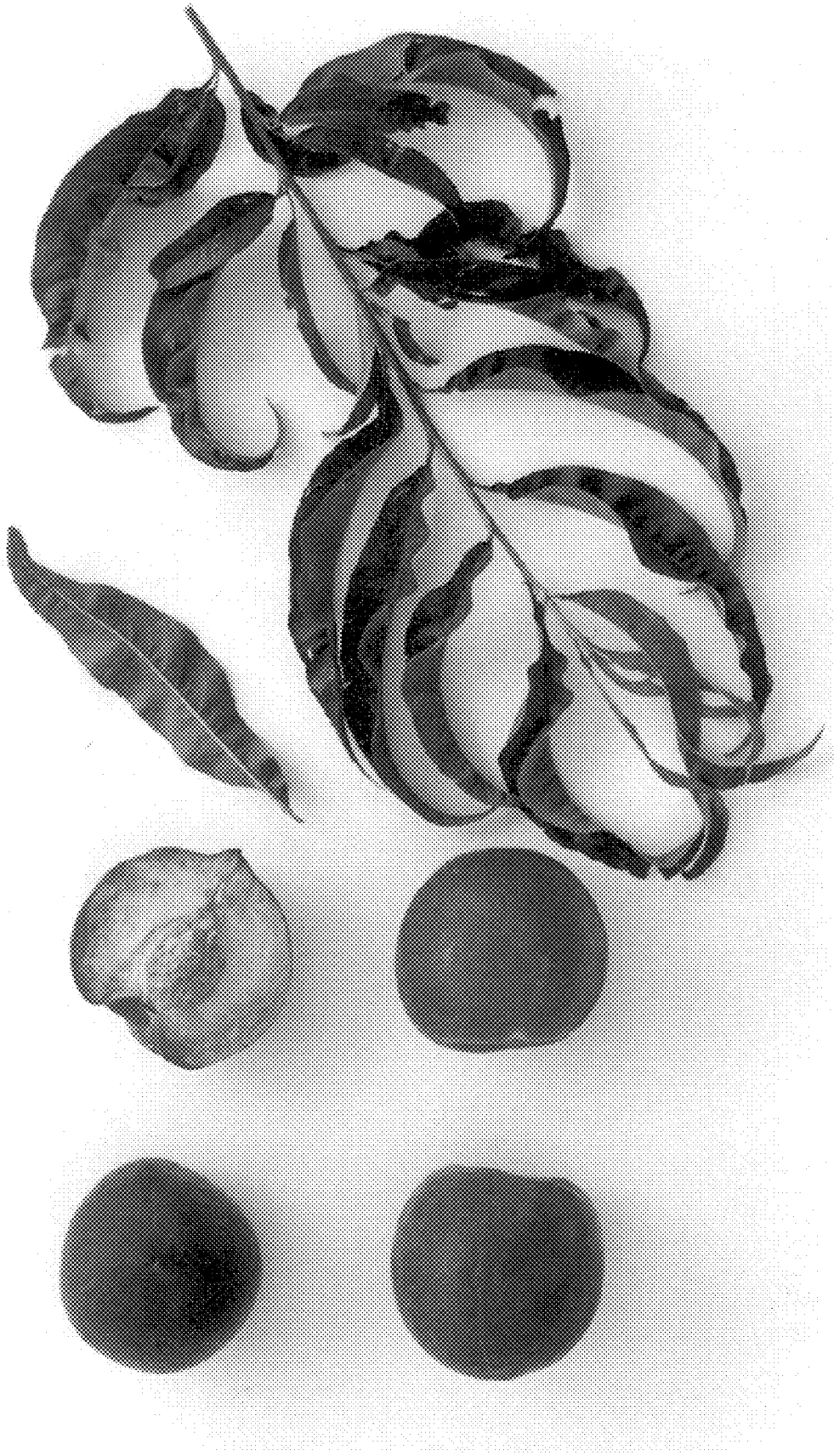

* * * * *